United States Patent [19]

Barcza

[11] Patent Number: 4,824,950

[45] Date of Patent: Apr. 25, 1989

[54] CHIRAL STATIONARY PHASES AND COLUMNS FOR CHROMATOGRAPHIC RESOLUTION

[75] Inventor: Sandor Barcza, Mountain Lakes, N.J.

[73] Assignee: Sandoz Pharm. Corp., E. Hanover, N.J.

[21] Appl. No.: 92,834

[22] Filed: Sep. 3, 1987

Related U.S. Application Data

[63] Continuation-in-part of Ser. No. 776,251, Sep. 16, 1985, abandoned.

[51] Int. Cl.[4] .......................... C07F 7/02; C07F 7/10; C07F 7/08; C07F 5/06

[52] U.S. Cl. ...................... 546/14; 556/173; 556/400; 556/418; 556/419; 556/420; 556/421; 556/422; 556/438; 556/440

[58] Field of Search ............... 556/173, 400, 418, 419, 556/420, 421, 422, 438, 440; 546/14

[56] References Cited

U.S. PATENT DOCUMENTS

| | | | |
|---|---|---|---|
| 4,302,594 | 11/1981 | Berenguer et al. | 556/400 X |
| 4,448,694 | 5/1984 | Plueddemann | 556/400 X |
| 4,474,704 | 10/1984 | Sawicki | 556/400 X |

Primary Examiner—Paul F. Shaver
Attorney, Agent, or Firm—Gerald D. Sharkin; Robert S. Honor; Walter F. Jewell

[57] ABSTRACT

This invention relates to chiral compositions.

13 Claims, No Drawings

CHIRAL STATIONARY PHASES AND COLUMNS FOR CHROMATOGRAPHIC RESOLUTION

This application is a continuation-in-part of U.S. Ser. No. 06/776,251, filed 09/16/85, now abandoned.

This invention relates to chiral compositions. In particular aspect it relates to chiral (optically active) chromatography columns for the separation of stereoisomers, particularly enantiomers.

Chromatographic resolution with columns containing chiral molecules bound to the surface of the stationary phase, has proven useful for the separation of optical isomers (enantiomers). For example, in the pharmaceutical field the isomeric composition of medicaments is important for enantiomers that differ in potency, pharmacological actions, or plasma disposition kinetics.

The present invention is concerned with chromatographic stationary phases and columns having chiral moieties bound to the surface of the stationary phase via optionally substituted acylamide, urea, urethane, carboxamide, sulfamide, sulfonamide, phosamide, ester and carbonate linkages.

The compounds of this invention have a Support Unit, Anchor Unit, Extender Arm, Linkage Unit, Working Unit, and may be represented by the following structural formula:

$$A(-O-)_n Si\begin{smallmatrix}R_3\\ \\R_4\end{smallmatrix}-R_1-B-R_2 \quad (I)$$

wherein A represents a Support unit, which may be silica, alumina, glass (porous) beads, diatomaceous earth, or other siliceus solids;

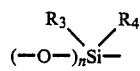

represents an Anchor unit where n represents an integer of from 1 to 3, $R_3$ and $R_4$ which can be the same or different each represents hydroxy, lower alkyl or alkoxy straight chain or branched having 1 to 4 carbon atoms, preferably unbranched, provided that when n=2 only $R_3$ occurs, when n=3 neither $R_3$ nor $R_4$ occurs;

$R_1$ (Extender arm) may be an aliphatic chain e.g., alkylene, olefinic or acetylenic, preferably unbranched and saturated, phenylene, arylene, having 1 to 18 carbon atoms, preferably 3 to 6 carbon atoms unbranched, or ether when $R_1$ may contain one —O—, with additionally at least a two carbon alkylene group between the —O— and the heteroatom which is part of the linkage unit;

B (Linkage unit) may be $-NR_5SO_2NR_5-$, $-NR_5CONR_5-$, $-NR_5CO-$, or $-CONR_5-$ or $-SO_2NR_5-$, $-NR_5SO_2-$, $-COO-$, $-OOC-$, $-OCOO-$, NCOO—, OOCN—; where each $R_5$ may be independently H, or lower alkyl having 1 to 4 carbon atoms, preferably unbranched, the preferred $R_5$ is H.

$R_2$ (Working unit) may be

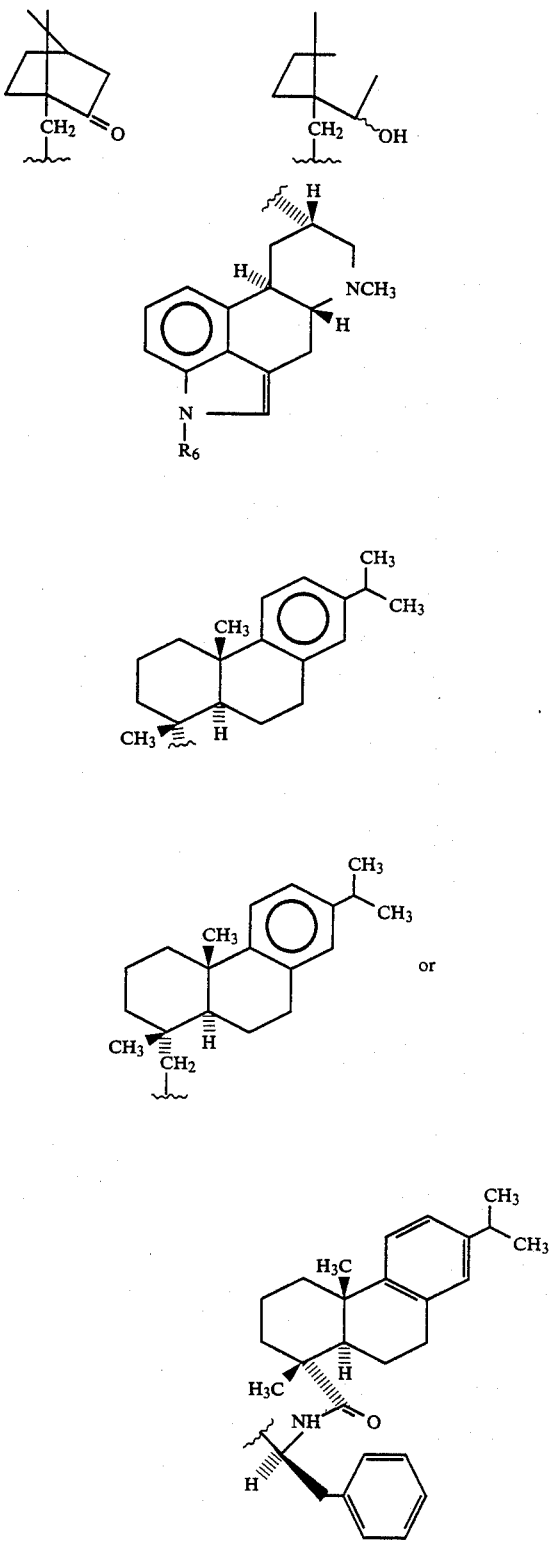

dehydroabietyl $R_6$ may be lower alkyl having 1 to 4 carbon atoms, or benzyl; B-$R_2$ may be The compounds of Formula I may be assembled in various sequences. The buildup of chiral derivatized solid surfaces can occur by two different strategies, both of which are within the scope of this invention.

1-Incremental bonding (binding) of components to the solid support, i.e. the bonded phase is assembled on the solid support. The growing assembly resides on the solid support.

2-Preassembly of the parts as soluble, non-polymeric species, with final linking of the preassembled agent to the solid support.

Combinations of 1 and 2 are also feasible.

Attaching the Anchor unit to the support is typically accomplished by methods used to form siloxane bonds, e.g. condensation of silanol groups with alkoxysilane, acyloxysilane, halosilane or silanol bearing moieties.

Establishing the Linkage (B) is typically accomplished by methods employed for acylations, e.g. reaction of activated acyl, e.g. acylhalide, anhydride, isocyanate and the like; with a nucleophile e.g. amine, alcohol, or mercaptan.

The compounds of formula I (e.g. N-[3-(hydroxydimethylsilyl)propyl]-N'-[[1,2,3,4,4a,9,10,10a-octahydro-1,4a-dimethyl-7-(1-methylethyl)phenanthren-1-yl]methyl]-sulfamide graft polymer with silicagel) may be prepared by reacting a compound of formula II (e.g. N-[3-(ethoxydimethylsilyl)propyl]-N'-[[1,2,3,4,4a,9,10,-10a-octahydro-1,4a-dimethyl-7-(1-methylethyl)phenanthren-1-yl]methyl]-[1R-(1ζ, 4aβ, 10aα]-Sulfamide, with silicagel.

$$(R_7-O-)_nSi-R_1-B-R_2 \quad \text{II}$$
$$\downarrow \text{Silicagel}$$
$$A(-O-)_nSi-R_1-B-R_2 \quad \text{I}$$

where $R_7$ is lower alkyl having 1–4 carbon atoms. The compounds of formula II may be prepared by reacting a compound of formula IV [$R_2Z$] with a compound of formula III $$[(R_7-O-)_nSi-R_1-y] \quad \text{or} \quad [A(-O-)_nSi-R_1-y]$$

A, n, $R_1$, $R_3$, $R_4$ are as defined above. Z and Y are functionalities sufficiently active or activated to establish linkage B; e.g.

(1) Z equals $NH_2$ and Y equals $NHSO_2Cl$ to form linkage B, being $-NHSO_2NH-$;

(2) Z equals NH and Y equals COCl to form linkage B being $-CONH-$; or (3) Z equals NCO (isocyanate) and Y equals $NH_2$ to form linkage B being $-NHCONH-$ i.e. urea linkage.

The following Examples illustrate the invention: All temperature values are stated in °C.

All reactions containing moisture sensitive components, e.g., acid chlorides, alkoxysilanes, were protected from atmospheric moisture by keeping them under dry nitrogen until workup, and by using dry solvents, e.g., toluene, xylene and dichloromethane from molecular sieves, etc.

Unless otherwise indicated, all evaporations, concentrations were performed from a bath at 40° and with vacuum of ~16 mmHg pressure. The drying of residues, cakes, solid products was in a vacuum oven with applied ~0.1 mmHg pressure.

EXAMPLE I

Preparation of Silicagel Particles

Silicagel, 25.0 g Licroprep ™ Si 60, for liquid chromatography, particle size 15 to 20 micrometers, by EM laboratories, Lot No. 9649812, Cat. No. 9336, reported surface area 500 m²/g, and 100 ml of 0.1N HCE were gently stirred at 90°–93° for 24 hours. The suspension was filtered and the silicagel was dried for 12 hours at 200° in vacuo, weight of dried material: 20.75 g.

Combustion microanalysis gave no significant carbon value:

% C: 0.023, 0.24; H: 0.68, 0.63; N: 0,0.

EXAMPLE II

Purification of Dehydroabietylamine

Crude commercial dehydroabietylamine, (234.4 g of Aldrich, Lot No. 071087 plus 266.8 g, Aldrich Cat. No. 10, 519-8) was dissolved in approx. 1l of methanol containing a small amount of diethyl ether. Gaseous HCl (67 g, theoretical is 64.1 g) was added with cooling. Addition of more ether caused the crystallization of the hydrochloride, crops of which were isolated upon adding more ether (2 crops) then adding toluene and removing the ether in vacuo

| Crop | Wt. g. | mp |
|---|---|---|
| 1 | 159.3 | (253)–258–262 (decomp) |
| 2 | 191.3 | (253)–258–262 (decomp) |
| 3 | 49.g | (252)–253–262 (decomp) |
| 4 | 84.0 | (253)–256–258 (decomp) |
| 5 | 35.5 | (250)–253–255 (decomp) |

The second crop (191.3 g) was shaken with an excess of dilute agneous sodium hydroxide and toluene, the organic phase was washed with water, dried over Na$_2$SO$_2$ and was concentrated to give 168.7 g of the free base (theory=169.6 g).

A 96.2-g sample of this material was dissolved in 200 ml of tetrahydrofuran (THF), and added to 497 ml of 0.98-M borane in THF at 0° to −10°. The temperature was allowed to rise to 20°, stirring was applied for 1 hour at 20°-25°, then the mixture was cooled to 0° and continuously (H$_2$ evolution) 20 ml of water was added at 0° to −10°. The hydrolyzed mixture was quenched with ice, sodium hydroxide solution and dichloromethane and sodium chloride solution. The organic phase was washed with two portions of dilute sodium hydroxide solution, dried over sodium sulfate, filtered and concentrated to lower volume. Toluene was added, concentration was continued until a heavy precipitate had formed, which was filtered off and dried: 60.8 g, mp (175)-176-177° (decomp). A second crop of 21.3 g was obtained, mp (177)-177.5-177.5° (decomp). The two crops were combined, dissolved in dichloromethane. Toluene was added and the solution was concentrated until a heavy precipitate had formed, which was filtered and dried: 51.1 g, mp 179-179 (decomp). A second crop weighed 24.2 g, mp 179.5 (decomp).

Both crops were dissolved in 700 ml of THF, and 350 and 2N HCl was added over a period of 0.75 hours, while the temperature rose to 33° and H gas evolved. After the gas evolution had stopped, the mixture was refluxed for 10 min., cooled and was mixed with ice and toluene and an excess of 2N sodium hydroxide. The toluene phase was washed with two portions of water, dried over Na$_2$SO$_4$, filtered and evaporated to the colorless oily free base. This was distilled using a kugelrohr, yielding 71.0 g of refined dehydroabietylamine, bp (evaporative) 127°-134° at 0.08 to 0.06 mmHg, mp (42.5)-43-44°, ultraviolet absorption in acetonitrile, (extinction coefficient at wavelength, nm): 10,140 at 218, 680 at 269 and 800 at 277 nm. Optical rotation: $[]^{25}_° = +52.9°$ (c=3.7, pyridine). Thinlayer analysis: single spot.

EXAMPLE III 3-(Dehydroabietylaminosulfonylamino)propyldimethylsiloxyderivatized silicagel To a solution of 8.5 g of dehydroabietylamine (29.8 mmol) in 200 ml of dichloromethane and 9.41 g (90.5 mmol) of triethylamine, precooled to −20°, 3.81 g (32.6 mmol) of chlorosulfonic acid was added, keeping the mixture at −20° to 0° during the exothermic addition. It was allowed to warm to room temperature during 1 hour, then stirred at room temperature for 1.5 hours more. The solvent was evaporated in vacuo, and to the semisolid residue 100 ml of toluene was added, producing a suspension. To this, 6.2 g (29.9 mmol) of phosphorous pentachloride was added, while the temperature rose to 29°. The mixture was heated at 90° for 1 hour, cooled, and the solids were filtered off. The filtrate was combined with a small amount of xylene to aid in the evaporation of phosphorous oxychloride by-product, and was concentrated and pumped under high vacuum to obtain 18.3 g of glassy residue containing the dehydroabietylsulfamoyl chloride.

This intermediate was dissolved in 150 ml of dichloromethane, cooled in a dry ice bath while 3.3 g (32.7 mmol) of triethylamine was added. The exotherm was controlled by keeping the mixture at −30° to −10°. Immediately 4.80 g (29.8 mmol) of 3-aminopropyldimethylethoxysilane was added in one portion. The temperature now at −50° was allowed to rise in 5 min. to 0°, then the mixture was stirred for 1 hour at 20°-25°.

To this mixture (minus 10-ml sample), containing the derivatized ethoxysilane, 10.0 g of dried silicagel was added. The suspension was heated at reflux for 4 hours, then 150 ml of toluene was added. Heating was continued while dichloromethane was allowed to distill off, the boiling point reaching 110°. The suspension was heated near reflux for 4 hours with occasional gentle stirring, then allowed to cool. Water (50 ml) was added, and the emulsion-suspension was filtered. The cake washed with water, methanol, acetonitrile and dichloromethane in succession, then it was vacuum dried at 75°-85° for 1 hour to give 14.37 g of the chiral, covalently derivatized solid.

Elemental microanalysis gave:

%, C: 15.8, 15.8; H 2.6, 2.6; N: 1.5, 1.5, containing the elements C, H, N in the correct ratio for the expected derivative.

EXAMPLE IV

3-Aminopropyldimethylsilyloxy-derivatized silicagel

The above material was prepared by heating 8.0 g of dried silicagel particles in 50 ml of toluene and 4.1 g of 3-aminopropyldimethylethoxysilane near reflux for 5.5 hours, cooling, filtering, washing and drying. The product weighed 8.39 g and had the following combustion elemental analysis:

% C: 7.6, 7.5; H: 1.6, 1.6; N; 1.0, 1.2.

EXAMPLE V 3-(Dehydroabietylaminosulfonylamino)propyldimethylsiloxyderivatized Silicagel. Alternate, Solid Phase Preparation To a solution of 5.0 g (17.5 mmol) of dehydroabietylamine in 6.0 g of triethylamine (59 mmol) and 150 ml of dichloromethane stirred at −20°, 2.1 g (18.0 mmol) of chlorosulfonic acid was added. The exothermic reaction was controlled by continued cooling, which kept the temperature at −20° to 0°. The mixture was allowed to warm to 20 during ¾ hr., stirred for ½ hr at 20°, then concentrated in vacuo. The resultant thick mass was combined with 100 ml of toluene, followed by 3.65 g (17.5 mmol) of phosphorous pentachloride. The mixture was heated for 1 hour at 80°, then cooled to 25°. A small amount of solids was filtered off, and the filtrate was concentrated to 9.67 g of glassy residue containing the dehydroabietylsulfamoylchloride and some residual phosphorous oxychloride. This concentrate was dissolved in 200 ml of dichloromethane, the solution was cooled to −20° and 2.3 g (22.8 mmol) of triethylamine was added. Cooling kept the temperature between −20° and 0° (addition exothermic). Immediately an amount 7.91 g of 3-aminopropyldimethylsilyloxy-derivatized silicagel particles was added. The mixture was stirred for 4 hours at 20°-25° with a teflon paddle stirrer, at slow speed so as to avoid damaging the silicagel particles by grinding action. Water (60 ml) was added and stirring was continued for 0.5 hour. The suspension was filtered, and the cake was washed in succession with methanol, water, methanol, acetonitrile and dichloromethane and dried at 80° in vacuo for 1 hour, to produce 9.47 g of 3-(dehydroabietylaminosulfonylamino)propyldimethylsiloxy-derivatized silicagel.

This product had the following elemental combustion elemental analysis:

% C: 17.7, 18.1; H: 3.2, 3.3; N: 1.9, 1.9.

EXAMPLE VI

Covalently Bonded Chiral Aminoergolene Derivatized Silicagel

To a solution of 6.57 g (37 mmol) of 3-isocyanato-propyldimethyl-chlorosilane in 200 ml of abs. (distilled from LiAlH$_4$) tetrahydrofuran, 3.74 g (37 mmol) of triethylamine was added at a temperature below −40° C., followed by the gradual addition of 1.18 g (37 mmol) of methanol with good stirring, at −55° to −60°. A heavy precipitate of triethylamine hydrochloride resulted.

The mixture, now containing the methoxysilane intermediate, was allowed to warm to 20°, after which 9.44 g (37 mmol) of the aminoergolene was added at 15° to 22°. The mixture was heated to near reflux for 10 min., then allowed to cool to 35°.

To this mixture, now containing the urea N-[3-(methoxydimethylsilyl)-propyl]-N'-8-ergolene-yl urea, 12.5 g of silicagel particles was added. The slurry was heated at 60° to 65° for 0.5 hour.

Throughout the entire experiment before workup, moisture was rigorously excluded. Dry nitrogen gas was applied as the atmosphere over the reaction mixture. A Teflon paddle stirrer was employed with gentle stirring in order to minimize breaking up of silicagel particles by grinding action.

To the reaction mixture, 100 ml of toluene was added, heating was increased to cause gentle distillation of the more volatile tetrahydrofuran solvent and methanol by-product. Additional 50 to 100 ml of toluene was added, and the heating was continued, collecting distillate until the boiling point reached 106°. The mixture was heated at 100°-110° for 1 hour longer, then allowed to cool to 25°.

Water (100 ml) was added, the suspension was filtered, and the filter cake was washed with water, methanol, acetonitrile and dichloromethane, in this order. The cake was dried in vacuo at 60°-70° for 1.5 hours to yield 15.45 g of silicagel covalently derivatized with chiral aminoergolene.

Analysis (%): C: 14.8; H: 2.35.

EXAMPLE VII

Chiral, Covalently Bonded Camphorsulfonamide Derivatized Silicagel

To a solution of 8.43 g (33.6 mmol) of d-10-camphorsulfonyl chloride in 150 ml of dry dichloromethane under a dry nitrogen atmosphere a mixture of 3.9 g (38.6 mmol) of triethylamine and 6.0 g, (32.8 mmol, 88%) of 3-aminopropyl-dimethyl-ethoxysilane was added followed by 20 ml of dichloromethane, beginning at +2° C. The temperature rose to 18° during the less than 5-min addition, and was then kept at 20°-25° for 0.5 hour.

Subsequently, 13.0 g of silicagel particles was added. The silicagel used was Art. 9336 Lichroprep Si 60, particle size 15-25 micrometer, surface area 500 m$^2$/g, dried for 12 hours in vacuo at 200°.

The slurry was heated to reflux, 150 ml of toluene was added, the temperature was allowed to rise to a boiling point of 109° while dichloromethane and ethanol distilled off. Gentle stirring with a paddle stirrer was applied to prevent bumping, and damage to the particles.

The mixture was cooled, 50 ml of water was added, and the slurry was filtered. The cake was washed with water, methanol, acetonitrile and dichloromethane, in this order, was vacuum dried at 75°-80° for 1 hour to yield 15.16 g of covalently derivatized product. Combustion elemental microanalysis gave, %,: C: 9.25; H: 2.05; N: 0.90; S: 1.01.

EXAMPLE VIII

Chiral, Covalently Bonded Dehydroabetic Acid Derivatized Silicagel

To a solution of 4.0 g (13.3 mmol) of dehydroabietic acid and 0.05 ml of N,N-dimethylformamide in 100 ml of dry toluene 2.5 ml of thionylchloride was added at 10°-25° The mixture was stirred until a sample, evaporated and combined with methanol, showed by thin-layer chromatogram to have been completely convereted to the acid chloride (Cf. spot for methyl ester versus starting free acid).

The solution of the acid chloride was concentrated in vacuo, with minimum exposure to moisture. The residue, taken up in 50 ml of dry dichloromethane was added to a solution of 2.0 ml of triethylamine (14.4 mmol) and 2.25 g of 3-aminopropyldimethyl-ethoxysilane in 50 ml of dry dichloromethane at 0°-25°. The resultant mixture was stirred at 20°-25° for 3 hours.

Subsequently, it was combined with 12.0 g of silicagel (Lichroprep Si 60, 15-25 microns, 500 m$^2$/g, dried, 200°, 12 hour vacuum). The suspension was brought to reflux, the low boiling components being distilled off while 150 ml of dry toluene was added. After the gently stirred (paddle stirrer) mixture reached the boiling point of toluene, it was cooled, combined with 50 ml of water, stirred and filtered. The cake was washed successively with water, methanol, acetonitrile and dichloromethane, dried in vacuo at 70°-80° for 2 hours to give 14.77 g of covalently bonded chiral derivatized silicagel.

EXAMPLE IX

A chiral liquid chromatographic column was prepared as follows:

Approximately 7 micron spherical particles of the compound,

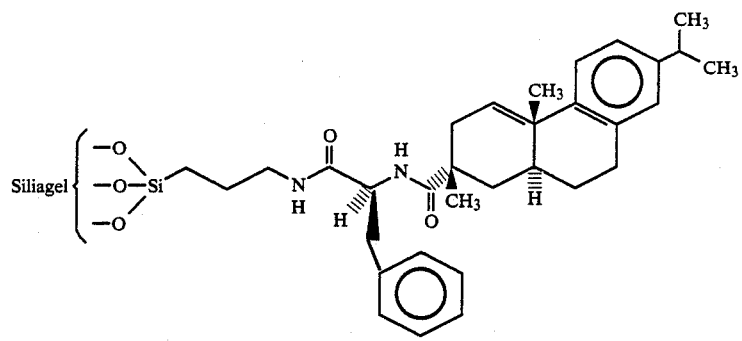

were conventionally slurry packed into a 4.6 mm×15 cm column, washed with 50 ml of 2-propanol, and then equilibrated with 90% hexane: 10% isopropanol.

Racemic mixtures of the following compounds were added by injection onto the column:

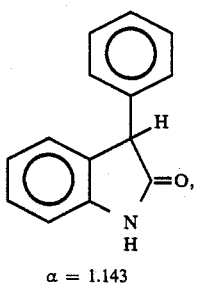
α = 1.143

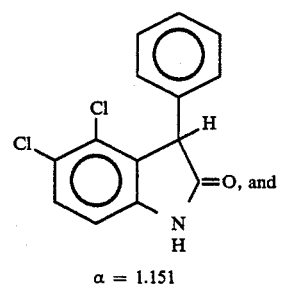
α = 1.151

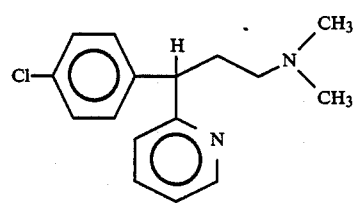

The individual enantiomers were separated under both normal phase and reverse conditions. Detection was by ultraviolet light at 254 nm at a scale of 0.128 absorbance units.

Normal phase conditions:
90% hexane: 10% isopropanol at a flow rate of 1 ml/min.
Reverse phase conditions:
75% methanol: 25% water at a flow rate of 1 ml/min.

EXAMPLE X

A chiral liquid chromatographic column was prepared as described in Example IX. The column was packed with the compound,

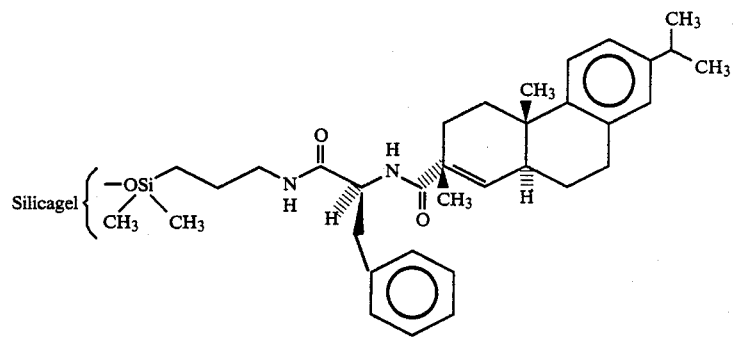

Racemic mixtures of

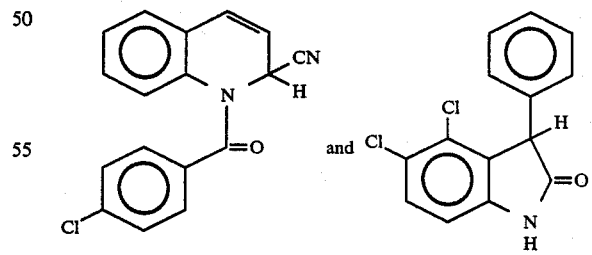

were added, by injection onto the column and separated as individual enantiomers, using the normal phase conditions of Example IX.

EXAMPLE XI

A chiral liquid chromatographic column was prepared as described in Example IX. The column was packed with compound,

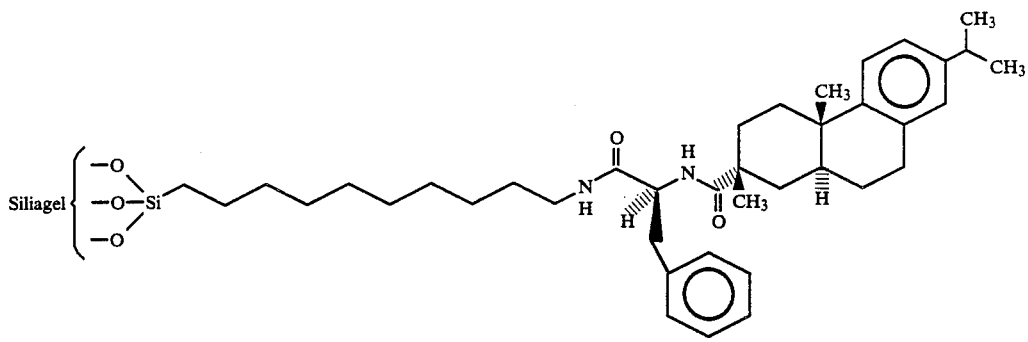

A racemic mixtures of

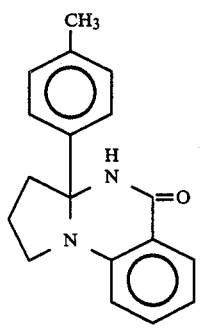

was added, by injection, onto the column and separated as individual enantimoers using the normal phase conditions of Example IX.

EXAMPLE XII

A chiral liquid chromatographic column was prepared as described in Example IX. The column was packed with the compound,

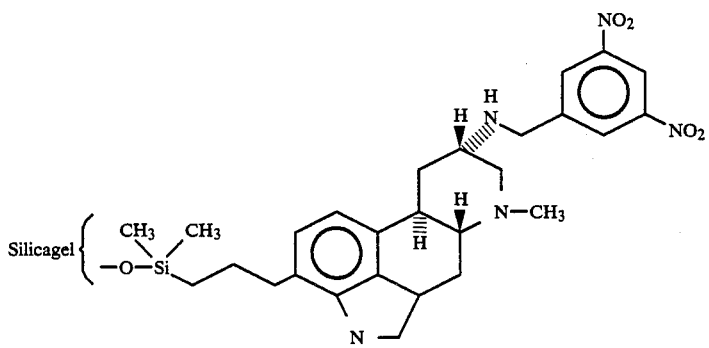

A racemic mixture of

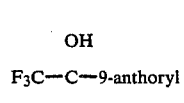

OH
F$_3$C—C—9-anthoryl
H was added, by injection, onto the column and separated as individual enantimores using the normal phase conditions of Example IX.

EXAMPLE XIII

A chiral liquid chromatographic column was prepared as described in Example IX. the column was packed with the compound,

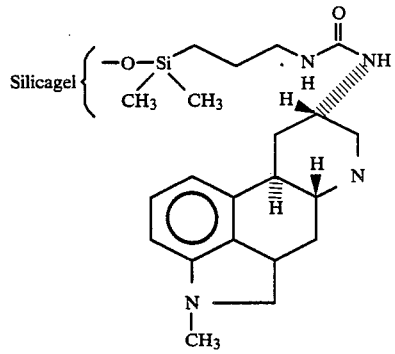

Racemic mixtures of

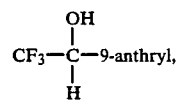

OH
CF$_3$—C—9-anthryl,
H 1-phenyl-propanol-1; 1-phenyl-ethanol, and

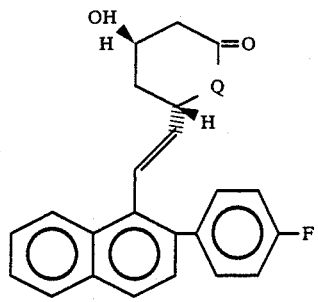

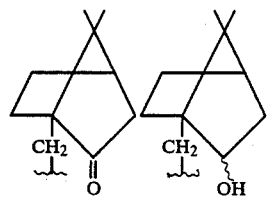

were added, by injection, onto the column and separated as individual enantiomers using normal phase conditions using 70% hexane: 20% dichloromethane:
10% acetonitrile, at a flow rate of 3 ml/min.
Detection was by ultraviolet light at 254 nm.

What is claimed is;

1. A composition of the formula,

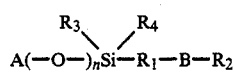

(I)

wherein
- A may be silica, alumina, glass beads, diatomaceous earth, or other siliceous solids;
- n represents an integer of from 1 to 3, $R_3$ and $R_4$ which can be the same or different each represents hydroxy, lower alkyl or alkoxy straight chain or branched having 1 to 4 carbon atoms, preferably unbranched, provided that when n=2 only $R_3$ occurs, when n=3 neither $R_3$ nor $R_4$ occurs;
- $R_1$ may be an aliphatic chain having 1 to 18 carbon atoms, phenylene, arylene or ether when $R_1$ may contain one —O—, with additionally at least two carbon alkylene group between the —O— and the heteroatom which is part of the B unit;
- B may be —NR$_5$SO$_2$NR$_5$—, —NR$_5$CONR$_5$—, —NR$_5$CO—, or —CONR$_5$— or —SO$_2$NR$_5$—, —NR$_5$SO$_2$—, —COO—, —OOC—, —OCOO, NCOO—, OOCN—;

where each $R_5$ may be independently H, or lower alkyl having 1 to 4 carbon atoms; and $R_2$ may be

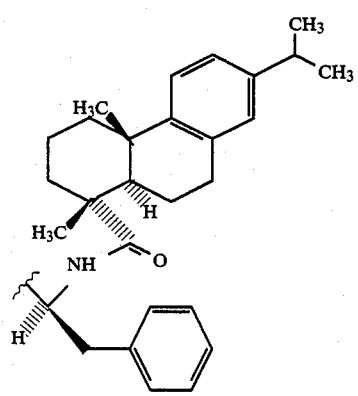

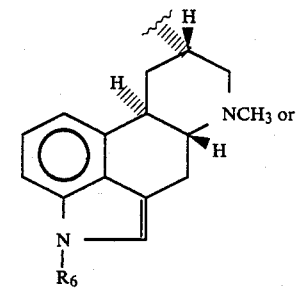

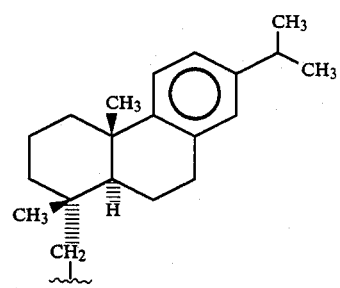

where $R_6$ may be lower alkyl having 1 to 4 carbon atoms, or benzyl; B-$R_2$ may be

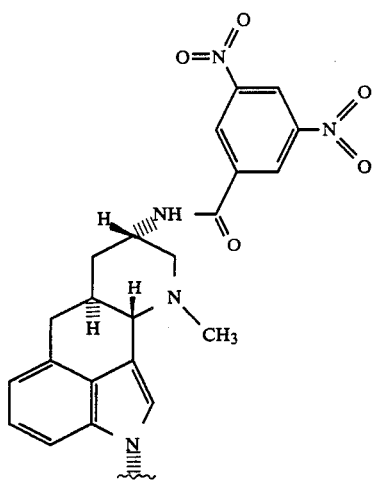

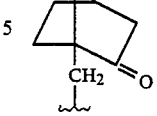

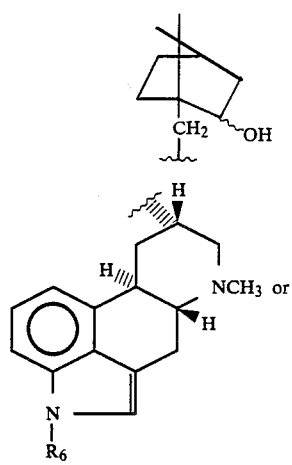

2. The composition according to claim 1 wherein $R_3$ and $R_4$ equal $CH_3$, and n equals 1.

3. The composition according to claim 1 wherein n equals 3.

4. The composition according to claim 1 wherein 3 equals —$NH_5SO_2NR_5$—.

5. The composition according to claim 1 wherein $R_2$ equals

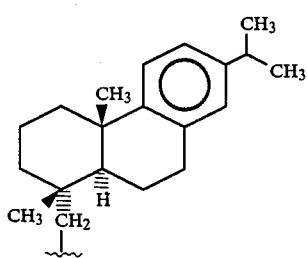

6. The composition according to claim 1 wherein B equals —$NR_5CO$—, or —$CONR_5$—.

7. The composition according to claim 1 wherein $R_5$ equals H.

8. The composition according to claim 1 wherein $R_2$ equals

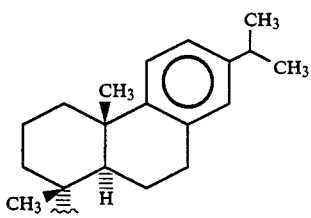

9. The composition of claim 1 which is 3-(Dehydroabietylaminosulfonylamino)propyldimethylsiloxy-derivatized silicagel.

10. The composition of claim 1 which is 3-(Dehydroabietylaminosulfonylamino)propyldimethylsiloxy-derivatized silicagel Alternate, Solid Phase Preparation.

11. The composition of claim 1 which is Covalently Bonded Chiral Aminoergolene Derivatized Silicagel.

12. The composition of claim 1 which is Chiral, Covalently Bonded Camphorsulfonamide Derivatized Silicagel.

13. The composition of claim 1 which is Chiral, Covalently Bonded Dehydroabetic Acid Derivatized Silicagel.

* * * * *